US008333739B2

(12) United States Patent
Møller (10) Patent No.: US 8,333,739 B2
(45) Date of Patent: *Dec. 18, 2012

(54) INJECTION DEVICE (75) Inventor: Claus Schmidt Møller, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 392 days.

This patent is subject to a terminal disclaimer.

(21) Appl. No.: 11/931,010

(22) Filed: Oct. 31, 2007

(65) Prior Publication Data

US 2008/0065026 A1   Mar. 13, 2008

Related U.S. Application Data (63) Continuation of application No. 11/765,789, filed on Jun. 20, 2007, now Pat. No. 8,202,256, which is a continuation of application No. 10/667,040, filed on Sep. 22, 2003, now Pat. No. 7,241,278, which is a continuation of application No. 09/882,536, filed on Jun. 14, 2001, now Pat. No. 6,663,602.

(60) Provisional application No. 60/275,790, filed on Mar. 14, 2001, provisional application No. 60/214,470, filed on Jun. 27, 2000.

(30) Foreign Application Priority Data

Jun. 16, 2000   (DK) ........................... PA 2000 00932
Mar. 7, 2001    (DK) ........................... PA 2001 00372

(51) Int. Cl.
*A61M 5/00* (2006.01)

(52) U.S. Cl. ......... 604/207; 604/209; 604/211; 604/224

(58) Field of Classification Search .......... 604/207–211, 604/181, 187, 218, 224
See application file for complete search history.

(56) References Cited

U.S. PATENT DOCUMENTS

| 854,399 A | 5/1907 | Bridge |
| 2,392,196 A | 2/1946 | Smith |
| 2,956,563 A | 10/1960 | Sarnoff |
| 3,110,310 A | 11/1963 | Cislak |

(Continued)

FOREIGN PATENT DOCUMENTS

AU   2003232576   1/2004

(Continued)

OTHER PUBLICATIONS

English Abstract of DE10201875 Published May 22, 2003.

(Continued)

*Primary Examiner* — Theodore Stigell
(74) *Attorney, Agent, or Firm* — Marc A. Began; Wesley A. Nicolas; Reza Green (57) ABSTRACT A medication dispensing device with a housing and a member wherein the member is moveable in a distal direction is useful in delivering medication to a patient. A fluid container can be used with the device and often has a moveable piston at one end and an outlet at the other. The member receives a force from a user and drives the piston in the distal direction to expel medication. A intermediate system is disposed between the member and the piston including a gear set that has a pinion in meshed engagement with a rack. The system allows the member to move a greater distance than the piston moves thereby increasing the force on the piston.

6 Claims, 4 Drawing Sheets

U.S. PATENT DOCUMENTS

| | | |
|---|---|---|
| 3,115,135 A | 12/1963 | Sarnoff |
| 3,144,178 A | 8/1964 | Sarnoff et al. |
| 3,556,099 A | 1/1971 | Knight et al. |
| 3,729,003 A | 4/1973 | Hurschman |
| 3,880,162 A | 4/1975 | Simmons |
| 3,944,843 A | 3/1976 | Vaz Martins |
| 4,026,288 A | 5/1977 | Costa et al. |
| 4,231,368 A | 11/1980 | Becker |
| 4,275,727 A | 6/1981 | Keeri-Szanto |
| 4,277,227 A | 7/1981 | Jenkins |
| 4,298,000 A | 11/1981 | Thill et al. |
| 4,300,554 A | 11/1981 | Hessberg et al. |
| 4,313,439 A | 2/1982 | Babb et al. |
| 4,314,556 A | 2/1982 | Ma |
| 4,368,731 A | 1/1983 | Schramm |
| RE31,315 E | 7/1983 | Jenkins et al. |
| 4,393,723 A | 7/1983 | Brand |
| 4,430,079 A | 2/1984 | Thill et al. |
| 4,465,478 A | 8/1984 | Sabelman et al. |
| 4,470,317 A | 9/1984 | Sabloewski |
| 4,493,704 A | 1/1985 | Beard et al. |
| 4,498,904 A | 2/1985 | Turner et al. |
| 4,515,584 A | 5/1985 | Abe et al. |
| 4,568,335 A | 2/1986 | Updike et al. |
| 4,585,439 A | 4/1986 | Michel |
| 4,634,431 A | 1/1987 | Whitney et al. |
| 4,676,122 A | 6/1987 | Szabo et al. |
| 4,749,109 A | 6/1988 | Kamen |
| 4,812,724 A | 3/1989 | Langer et al. |
| 4,833,379 A | 5/1989 | Kaibel et al. |
| 4,838,860 A | 6/1989 | Groshong et al. |
| 4,865,591 A | 9/1989 | Sams |
| 4,871,351 A | 10/1989 | Feingold |
| 4,883,472 A | 11/1989 | Michel |
| 4,893,291 A | 1/1990 | Bick et al. |
| 4,898,578 A | 2/1990 | Rubalcaba |
| 4,919,596 A | 4/1990 | Slate et al. |
| 4,936,833 A | 6/1990 | Sams |
| 4,950,246 A | 8/1990 | Muller |
| 4,973,318 A | 11/1990 | Holm |
| 4,988,337 A | 1/1991 | Ito |
| 4,994,033 A | 2/1991 | Shockey et al. |
| 5,000,744 A | 3/1991 | Hoffman et al. |
| 5,002,537 A | 3/1991 | Hoffman et al. |
| 5,064,098 A | 11/1991 | Hutter et al. |
| 5,078,698 A | 1/1992 | Stiehl et al. |
| 5,104,380 A | 4/1992 | Holman et al. |
| 5,104,388 A | 4/1992 | Quackenbush |
| 5,112,317 A | 5/1992 | Michel |
| 5,113,869 A | 5/1992 | Nappholz et al. |
| 5,114,406 A | 5/1992 | Gabriel et al. |
| 5,122,317 A | 6/1992 | Chen et al. |
| 5,135,485 A | 8/1992 | Cohen et al. |
| 5,163,904 A | 11/1992 | Lampropoulos et al. |
| 5,176,646 A | 1/1993 | Kuroda |
| 5,207,752 A | 5/1993 | Sorenson et al. |
| 5,221,268 A | 6/1993 | Barton et al. |
| 5,226,342 A | 7/1993 | Panin |
| 5,226,895 A | 7/1993 | Harris |
| 5,226,896 A | 7/1993 | Harris |
| 5,244,461 A | 9/1993 | Derlien |
| 5,244,465 A | 9/1993 | Michel |
| 5,246,417 A | 9/1993 | Haak et al. |
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,284,480 A | 2/1994 | Porter et al. |
| 5,292,976 A | 3/1994 | Dessau et al. |
| 5,295,976 A | 3/1994 | Harris |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,368,572 A | 11/1994 | Shirota |
| 5,370,629 A | 12/1994 | Michel et al. |
| 5,378,233 A | 1/1995 | Haber et al. |
| 5,383,856 A | 1/1995 | Bersin |
| 5,383,865 A | 1/1995 | Michel |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,480,387 A | 1/1996 | Gabriel et al. |
| 5,492,534 A | 2/1996 | Athayde et al. |
| 5,496,286 A | 3/1996 | Stiehl et al. |
| 5,505,697 A | 4/1996 | McKinnon, Jr. |
| 5,505,704 A | 4/1996 | Pawelka et al. |
| 5,536,249 A | 7/1996 | Castellano et al. |
| 5,546,932 A | 8/1996 | Galli |
| 5,549,575 A | 8/1996 | Giambattista |
| 5,573,729 A | 11/1996 | Belgardt et al. |
| 5,582,598 A | 12/1996 | Chanoch |
| 5,584,815 A | 12/1996 | Pawelka et al. |
| 5,591,136 A | 1/1997 | Gabriel |
| 5,593,390 A | 1/1997 | Castellano et al. |
| 5,599,314 A | 2/1997 | Neill |
| 5,611,783 A | 3/1997 | Mikkelsen |
| 5,611,784 A | 3/1997 | Barresi et al. |
| 5,626,566 A | 5/1997 | Petersen et al. |
| 5,628,309 A | 5/1997 | Brown |
| 5,637,095 A | 6/1997 | Nason et al. |
| 5,645,052 A | 7/1997 | Kersey |
| 5,662,612 A | 9/1997 | Niehoff |
| 5,674,204 A | 10/1997 | Chanoch |
| 5,679,111 A | 10/1997 | Hertman et al. |
| 5,681,285 A | 10/1997 | Ford et al. |
| 5,685,864 A | 11/1997 | Shanley et al. |
| 5,688,251 A | 11/1997 | Chanoch |
| 5,709,662 A | 1/1998 | Olive et al. |
| 5,716,990 A | 2/1998 | Bagshawe et al. |
| 5,720,733 A | 2/1998 | Brown |
| 5,725,508 A | 3/1998 | Chanoch |
| 5,728,074 A | 3/1998 | Castellano et al. |
| 5,728,559 A | 3/1998 | Nilsson et al. |
| 5,741,211 A | 4/1998 | Renirie et al. |
| 5,743,889 A | 4/1998 | Sams |
| 5,755,692 A | 5/1998 | Manicom |
| 5,782,633 A | 7/1998 | Mühlbauer |
| 5,807,334 A | 9/1998 | Hodosh et al. |
| 5,814,022 A | 9/1998 | Antanavich et al. |
| 5,820,602 A | 10/1998 | Kovelman et al. |
| 5,823,998 A | 10/1998 | Yamagata |
| 5,827,232 A | 10/1998 | Chanoch |
| 5,830,194 A | 11/1998 | Anwar et al. |
| 5,843,036 A | 12/1998 | Olive et al. |
| 5,879,360 A | 3/1999 | Crankshaw |
| 5,879,630 A | 3/1999 | Lescouzeres et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,933,671 A | 8/1999 | Stephany et al. |
| 5,938,642 A | 8/1999 | Burroughs |
| 5,947,934 A | 9/1999 | Hansen et al. |
| 5,951,530 A | 9/1999 | Steengaard |
| 5,954,689 A | 9/1999 | Poulsen |
| 5,954,700 A | 9/1999 | Kovelman |
| 5,957,889 A | 9/1999 | Poulsen et al. |
| 5,961,496 A | 10/1999 | Nielsen et al. |
| 5,971,963 A | 10/1999 | Choi |
| 5,980,491 A | 11/1999 | Hansen |
| 5,984,900 A | 11/1999 | Mikkelson |
| 5,989,221 A | 11/1999 | Hjertman |
| 5,998,989 A | 12/1999 | Lohberg |
| 6,003,736 A * | 12/1999 | Ljunggren .................... 222/309 |
| 6,004,297 A | 12/1999 | Steenfeldt-Jensen et al. |
| 6,010,485 A | 1/2000 | Buch-Rasmussen et al. |
| 6,019,745 A | 2/2000 | Gray |
| 6,033,376 A | 3/2000 | Rockley |
| 6,033,377 A | 3/2000 | Rasmussen |
| 6,036,675 A | 3/2000 | Thorne et al. |
| 6,048,336 A | 4/2000 | Gabriel |
| 6,074,372 A | 6/2000 | Hansen et al. |

| | | | | | | |
|---|---|---|---|---|---|---|
| 6,083,197 | A | 7/2000 | Umbaugh | 2002/0020654 A1 | 2/2002 | Eilersen |
| 6,086,567 | A | 7/2000 | Kirchhofer et al. | 2002/0049415 A1 | 4/2002 | Fukuda |
| 6,096,010 | A | 8/2000 | Walters | 2002/0052578 A1 | 5/2002 | Moller |
| 6,110,148 | A | 8/2000 | Brown et al. | 2002/0077852 A1 | 6/2002 | Ford et al. |
| 6,110,149 | A | 8/2000 | Klitgaard | 2002/0107486 A1 | 8/2002 | Munk |
| 6,129,080 | A | 10/2000 | Pitcher et al. | 2002/0120235 A1 | 8/2002 | Enggaard |
| 6,146,361 | A | 11/2000 | DiBiasi et al. | 2002/0165500 A1 | 11/2002 | Bechtold et al. |
| 6,159,161 | A | 12/2000 | Hodosh | 2002/0173752 A1 | 11/2002 | Polzin |
| 6,161,364 | A | 12/2000 | Kolberg | 2002/0188250 A1 | 12/2002 | Landau et al. |
| 6,193,698 | B1 | 2/2001 | Kirchhofer | 2003/0009133 A1 | 1/2003 | Ramey |
| 6,221,046 | B1 | 4/2001 | Burroughs | 2003/0039679 A1 | 2/2003 | Duirs |
| 6,221,053 | B1 | 4/2001 | Walters | 2003/0073954 A1 | 4/2003 | Moberg et al. |
| 6,231,540 | B1 | 5/2001 | Smedegaard | 2003/0114800 A1 | 6/2003 | Veasey et al. |
| 6,235,004 | B1 | 5/2001 | Steenfeldt-Jensen et al. | 2003/0172924 A1 | 9/2003 | Staniforth |
| 6,245,046 | B1 | 6/2001 | Sibbitt | 2003/0176871 A1 | 9/2003 | Pavlov et al. |
| 6,248,090 | B1 | 6/2001 | Jensen et al. | 2003/0216663 A1 | 11/2003 | Willuhn et al. |
| 6,248,095 | B1 | 6/2001 | Giambattista et al. | 2003/0233075 A1 | 12/2003 | Huegli et al. |
| 6,258,062 | B1 | 7/2001 | Thielen et al. | 2004/0010204 A1 | 1/2004 | Weber et al. |
| 6,268,722 | B1 | 7/2001 | Kogure et al. | 2004/0024361 A1 | 2/2004 | Fago |
| 6,269,340 | B1 | 7/2001 | Ford et al. | 2004/0051368 A1 | 3/2004 | Caputo et al. |
| 6,277,097 | B1 | 8/2001 | Mikkelsen | 2004/0054326 A1 | 3/2004 | Hommann et al. |
| 6,277,098 | B1 | 8/2001 | Klitmose et al. | 2004/0059299 A1 | 3/2004 | Moller |
| 6,281,225 | B1 | 8/2001 | Hearst et al. | 2004/0097879 A1 | 5/2004 | Woolston |
| 6,283,941 | B1 | 9/2001 | Schoenfeld | 2004/0108339 A1 | 6/2004 | Hansen et al. |
| 6,287,283 | B1 | 9/2001 | Ljunggreen | 2004/0158304 A1 | 8/2004 | Cory et al. |
| 6,302,869 | B1 | 10/2001 | Klitgaard | 2004/0171983 A1 | 9/2004 | Sparks et al. |
| 6,312,413 | B1 | 11/2001 | Jensen et al. | 2004/0186431 A1 | 9/2004 | Graf et al. |
| 6,340,357 | B1 | 1/2002 | Poulsen et al. | 2004/0207385 A1 | 10/2004 | Gafner et al. |
| 6,364,860 | B1 | 4/2002 | Steck et al. | 2004/0210199 A1 | 10/2004 | Atterbury et al. |
| 6,379,339 | B1 | 4/2002 | Klitgaard | 2004/0230157 A1 | 11/2004 | Perry et al. |
| 6,383,167 | B2 | 5/2002 | Kirchhofer | 2004/0236282 A1 | 11/2004 | Braithwaite |
| 6,391,005 | B1 | 5/2002 | Lum et al. | 2004/0249348 A1 | 12/2004 | Wimpenny et al. |
| 6,419,661 | B1 | 7/2002 | Kuhr et al. | 2004/0260247 A1 | 12/2004 | Veasey et al. |
| 6,514,230 | B1 | 2/2003 | Munk et al. | 2004/0267207 A1 | 12/2004 | Veasey et al. |
| 6,537,251 | B2 | 3/2003 | Klitmose | 2004/0267208 A1 | 12/2004 | Veasey et al. |
| 6,547,755 | B1 | 4/2003 | Lippe et al. | 2005/0004529 A1 | 1/2005 | Veasey et al. |
| 6,547,763 | B2 | 4/2003 | Steenfeldt-Jensen et al. | 2005/0019400 A1 | 1/2005 | Deveney et al. |
| 6,547,764 | B2 | 4/2003 | Larsen et al. | 2005/0033244 A1 | 2/2005 | Veasey et al. |
| 6,562,011 | B1 | 5/2003 | Buch-Rasmussen et al. | 2005/0055011 A1 | 3/2005 | Enggaard |
| 6,569,126 | B1 | 5/2003 | Poulsen et al. | 2005/0197625 A1 | 9/2005 | Haueter et al. |
| 6,582,404 | B1 | 6/2003 | Klitgaard | 2005/0205083 A1 | 9/2005 | Staniforth |
| 6,585,698 | B1 | 7/2003 | Packman et al. | 2005/0209570 A1 | 9/2005 | Møller |
| 6,599,272 | B1 | 7/2003 | Hjertman et al. | 2005/0268915 A1 | 12/2005 | Wassenaar |
| 6,605,067 | B1 | 8/2003 | Larsen | 2006/0118612 A1 | 6/2006 | Christoffersen et al. |
| 6,613,019 | B2 | 9/2003 | Munk | 2006/0258988 A1 | 11/2006 | Keitel et al. |
| 6,663,602 | B2 | 12/2003 | Moller | 2006/0264838 A1 | 11/2006 | Volckmann |
| 6,666,849 | B1 | 12/2003 | Marshall et al. | 2007/0093761 A1 | 4/2007 | Veasey |
| 6,673,033 | B1 | 1/2004 | Sciulli et al. | 2007/0244445 A1 | 10/2007 | Moller |
| 6,692,472 | B2 | 2/2004 | Hansen et al. | 2008/0065026 A1 | 3/2008 | Moller |
| 6,699,224 | B2 | 3/2004 | Kirchhofer et al. | 2008/0221530 A1 | 9/2008 | Glejbol et al. |
| 6,716,198 | B2 | 4/2004 | Larsen | 2008/0281275 A1 | 11/2008 | Moller |
| 6,726,661 | B2 | 4/2004 | Munk et al. | 2009/0043264 A1 | 2/2009 | Glejbol et al. |
| 6,752,798 | B2 | 6/2004 | McWethy et al. | 2009/0062748 A1 | 3/2009 | Moller et al. |
| 6,770,288 | B2 | 8/2004 | Duirs | 2011/0046565 A1 | 2/2011 | Radmer et al. |
| 6,796,970 | B1 | 9/2004 | Klitmose et al. | 2012/0095410 A1 | 4/2012 | Moller et al. |
| 6,852,404 | B2 | 2/2005 | Kuwajima et al. | | | |
| 6,887,238 | B2 | 5/2005 | Jahns et al. | | | |
| 6,893,415 | B2 | 5/2005 | Madsen et al. | | | |
| 6,899,698 | B2 | 5/2005 | Sams | | | |
| 6,899,699 | B2 | 5/2005 | Enggaard | | | |
| 6,945,961 | B2 | 9/2005 | Miller et al. | | | |
| 7,008,399 | B2 | 3/2006 | Larsen et al. | | | |
| 7,080,936 | B1 | 7/2006 | Simpson | | | |
| 7,090,662 | B2 | 8/2006 | Wimpenny et al. | | | |
| 7,094,221 | B2 | 8/2006 | Veasey et al. | | | |
| 7,104,972 | B2 | 9/2006 | Moller et al. | | | |
| 7,133,329 | B2 | 11/2006 | Skyggebjerg et al. | | | |
| 7,175,055 | B2 | 2/2007 | Hansen et al. | | | |
| 7,195,609 | B2 | 3/2007 | Huegli | | | |
| 7,195,616 | B2 | 3/2007 | Diller et al. | | | |
| 7,241,278 | B2 | 7/2007 | Moller | | | |
| 7,500,966 | B2 | 3/2009 | Hommann | | | |
| 7,678,084 | B2 | 3/2010 | Judson et al. | | | |
| 7,704,238 | B2 | 4/2010 | Diller et al. | | | |
| 2001/0034506 | A1 | 10/2001 | Hirschman et al. | | | |
| 2001/0053893 | A1 | 12/2001 | Larsen | | | |
| 2002/0002326 | A1 | 1/2002 | Causey, III et al. | | | |
| 2002/0007154 | A1 | 1/2002 | Hansen et al. | | | |
| 2002/0016571 | A1 | 2/2002 | Kirchhofer et al. | | | |

FOREIGN PATENT DOCUMENTS

| | | |
|---|---|---|
| BR | PI0613926 A2 | 2/2011 |
| CA | 2359375 | 7/2000 |
| DE | 3048135 | 7/1982 |
| DE | 3236374 | 4/1984 |
| DE | 3609555 A1 * | 9/1987 |
| DE | 3638984 | 5/1988 |
| DE | 3923079 | 1/1991 |
| DE | 4223958 | 1/1993 |
| DE | 4419235 | 12/1995 |
| DE | 19503230 | 8/1996 |
| DE | 29513214 | 2/1997 |
| DE | 19723647 | 12/1998 |
| DE | 19838760 | 4/2000 |
| DE | 29907880 | 9/2000 |
| DE | 10103287 | 8/2001 |
| DE | 10201875 | 5/2003 |
| DE | 10229122 | 2/2004 |
| DE | 20317377 | 4/2005 |
| DE | 102004046003 | 3/2006 |
| DK | 200100240 | 2/2001 |
| DK | 2005/00116 | 6/2005 |
| EP | 15617 | 9/1980 |

| | | | | | | |
|---|---|---|---|---|---|---|
| EP | 017318 | 10/1980 | | JP | 7-502678 | 3/1995 |
| EP | 0064858 | 11/1982 | | JP | 09166474 | 6/1997 |
| EP | 327810 | 8/1989 | | JP | 11511364 | 10/1999 |
| EP | 327910 | 8/1989 | | JP | 3017167 | 11/1999 |
| EP | 338806 | 10/1989 | | JP | 2000237308 | 9/2000 |
| EP | 0362484 | 4/1990 | | JP | 2002503122 A | 1/2002 |
| EP | 387854 | 9/1990 | | JP | 2003284777 | 10/2003 |
| EP | 422482 | 4/1991 | | JP | 2004-503303 | 2/2004 |
| EP | 454331 | 10/1991 | | JP | 2004503303 A | 2/2004 |
| EP | 498737 | 8/1992 | | JP | 2004-516895 | 6/2004 |
| EP | 879610 | 8/1992 | | JP | 2004533285 A | 11/2004 |
| EP | 0513128 | 11/1992 | | JP | 2005536300 A | 12/2005 |
| EP | 608343 | 4/1993 | | JP | 2006250582 | 9/2006 |
| EP | 554996 | 8/1993 | | JP | 2007-509662 | 4/2007 |
| EP | 594349 | 4/1994 | | RU | 2111019 | 5/1997 |
| EP | 615762 | 9/1994 | | RU | 2091087 | 9/1997 |
| EP | 513128 | 7/1995 | | RU | 2212254 | 9/2003 |
| EP | 0673482 | 9/1995 | | WO | WO8502256 | 5/1985 |
| EP | 679440 | 11/1995 | | WO | WO 87/02895 | 5/1987 |
| EP | 702970 | 3/1996 | | WO | WO 89/07463 | 8/1989 |
| EP | 0704225 A2 | 4/1996 | | WO | WO 90/09202 | 8/1990 |
| EP | 0708179 A2 | 4/1996 | | WO | WO 91/10460 | 7/1991 |
| EP | 1000631 | 10/1997 | | WO | WO 91/10677 | 7/1991 |
| EP | 554995 | 12/1997 | | WO | WO 91/14467 | 10/1991 |
| EP | 295075 | 12/1998 | | WO | WO9301573 | 1/1993 |
| EP | 897728 | 2/1999 | | WO | WO 93/03780 | 3/1993 |
| EP | 0937471 | 8/1999 | | WO | WO 93/07922 | 4/1993 |
| EP | 0937472 | 8/1999 | | WO | WO 9412228 | 6/1994 |
| EP | 1003581 | 8/1999 | | WO | WO9524233 | 9/1995 |
| EP | 956873 A2 | 11/1999 | | WO | WO 96/07443 | 3/1996 |
| EP | 1351732 | 1/2001 | | WO | WO 96/26754 | 9/1996 |
| EP | 1074273 | 2/2001 | | WO | WO 96/32973 | 10/1996 |
| EP | 1095668 | 5/2001 | | WO | WO 96/38190 | 12/1996 |
| EP | 1216717 A1 | 6/2002 | | WO | WO 97/07841 | 3/1997 |
| EP | 1216719 A1 | 6/2002 | | WO | WO 9710865 | 3/1997 |
| EP | 0747391 | 3/2004 | | WO | WO9730742 | 8/1997 |
| EP | 1462134 | 9/2004 | | WO | WO 97/34919 | 9/1997 |
| EP | 937476 | 1/2005 | | WO | WO 97/36626 | 10/1997 |
| EP | 1541185 | 6/2005 | | WO | WO 98/10813 | 3/1998 |
| EP | 1557163 | 7/2005 | | WO | 9856439 | 12/1998 |
| EP | 1557189 | 7/2005 | | WO | WO 98/56436 | 12/1998 |
| EP | 1 568 389 | 8/2005 | | WO | WO98/57688 | 12/1998 |
| EP | 1304129 | 11/2005 | | WO | WO9907425 | 2/1999 |
| EP | 1610848 | 4/2006 | | WO | WO 99/16487 | 4/1999 |
| EP | 1645301 | 4/2006 | | WO | WO9915214 | 4/1999 |
| EP | 1723977 | 11/2006 | | WO | WO 99/21598 | 5/1999 |
| EP | 1728529 | 12/2006 | | WO | WO 99/38554 | 8/1999 |
| EP | 1782853 | 5/2007 | | WO | WO 99/48546 | 9/1999 |
| EP | 1819382 | 8/2007 | | WO | WO9965548 | 12/1999 |
| EP | 2000161 | 12/2008 | | WO | 0015224 A1 | 3/2000 |
| EP | 2019701 A1 | 2/2009 | | WO | 0037098 A1 | 6/2000 |
| FR | 2583291 | 12/1986 | | WO | WO0037129 | 6/2000 |
| FR | 2622457 | 5/1989 | | WO | WO 00/51668 | 9/2000 |
| FR | 2697434 | 5/1994 | | WO | 01/10484 | 2/2001 |
| FR | 2740345 | 4/1997 | | WO | WO 01/19434 | 3/2001 |
| FR | 2767479 | 2/1999 | | WO | WO0126710 | 4/2001 |
| FR | 2857654 | 1/2005 | | WO | WO 01/30425 | 5/2001 |
| GB | 664044 | 1/1952 | | WO | WO0172361 | 10/2001 |
| GB | 2091107 | 7/1982 | | WO | WO 01/95959 | 12/2001 |
| GB | 2153445 | 8/1985 | | WO | WO0205876 | 1/2002 |
| GB | 2229497 | 9/1990 | | WO | WO0224257 | 3/2002 |
| GB | 2309644 | 8/1997 | | WO | WO 02/053214 | 7/2002 |
| GB | 0007071.4 | 3/2000 | | WO | WO02064196 | 8/2002 |
| IN | 165367 | 3/1986 | | WO | 02/076535 | 10/2002 |
| JP | 56-163486 | 12/1981 | | WO | 02/076537 | 10/2002 |
| JP | 57-000033 | 1/1982 | | WO | WO 2002/076536 | 10/2002 |
| JP | 01-100495 | 4/1989 | | WO | WO 02/092153 | 11/2002 |
| JP | 64-035671 | 6/1989 | | WO | 03/057286 A1 | 7/2003 |
| JP | 02071758 A | 3/1990 | | WO | WO03057283 | 7/2003 |
| JP | 02-126184 | 5/1990 | | WO | WO03063680 | 8/2003 |
| JP | 02-182267 | 7/1990 | | WO | WO9733638 | 9/2003 |
| JP | 4-224764 | 8/1992 | | WO | WO 03/080160 | 10/2003 |
| JP | 04256757 A | 9/1992 | | WO | WO03099357 | 12/2003 |
| JP | 4-507059 | 12/1992 | | WO | WO 2004/002556 | 1/2004 |
| JP | 05-337179 | 12/1993 | | WO | WO 2004/007002 | 1/2004 |
| JP | 06-055644 | 1/1994 | | WO | WO 2004004825 | 1/2004 |
| JP | 06-034825 | 2/1994 | | WO | WO 2004/024218 | 3/2004 |
| JP | 7-500039 | 3/1994 | | WO | WO 2004/028598 | 4/2004 |
| JP | 06-296691 | 10/1994 | | WO | WO 2004/035113 | 4/2004 |

| WO | WO 2004/078239 | 9/2004 |
| --- | --- | --- |
| WO | WO 2004/078240 | 9/2004 |
| WO | WO 2004/078241 | 9/2004 |
| WO | WO 2004078242 | 9/2004 |
| WO | WO2004080306 | 9/2004 |
| WO | WO2004084795 | 10/2004 |
| WO | 2004/093940 A2 | 11/2004 |
| WO | WO2004095379 | 11/2004 |
| WO | WO 2005018721 | 3/2005 |
| WO | WO 2005037352 | 4/2005 |
| WO | WO 2005/046770 | 5/2005 |
| WO | WO2005089835 | 9/2005 |
| WO | 2005097233 | 10/2005 |
| WO | 2005097240 | 10/2005 |
| WO | 2006/26754 A2 | 3/2006 |
| WO | 2006/037434 A1 | 4/2006 |
| WO | WO2006039930 | 4/2006 |
| WO | WO 2006/045528 | 5/2006 |
| WO | WO 2006/045529 | 5/2006 |
| WO | WO2006045425 | 5/2006 |
| WO | WO2006045525 | 5/2006 |
| WO | WO 2006/069454 | 7/2006 |
| WO | WO2006076921 | 7/2006 |
| WO | WO2006116997 | 11/2006 |
| WO | WO 2006/128794 | 12/2006 |
| WO | WO 2007/030957 | 3/2007 |
| WO | WO2007041843 | 4/2007 |
| WO | WO2007107558 | 9/2007 |
| WO | WO2007107561 | 9/2007 |
| WO | WO 2007/134954 | 11/2007 |
| WO | WO 2008/037801 | 4/2008 |
| WO | WO2008057223 | 5/2008 |

OTHER PUBLICATIONS

English Abstract of DE102004046003 Published Mar. 30, 2006.
English Abstract of DE19503230 Published Aug. 8, 1996.
English Abstract of DE 19838760 dated Apr. 20, 2000.
English Abstract of DE29513214 Published Feb. 13, 1997.
English Abstract of DE3236374 Published Apr. 5, 1984.
English Abstract of DE3923079 Published Jan. 24, 1991.
English Abstract of EP387854 Published Sep. 19, 1990.
English Abstract of EP422482 Published Apr. 17, 1991.
English Abstract of FR2622457 Published May 5, 1989.
English Abstract of FR2740345 Published Apr. 30, 1997.
English Abstract of IN165367 Published Mar. 20, 1986.
English Abstract of JP01-100495 Published Apr. 18, 1989.
Machine Translation of JP09166474 Published Jun. 24, 1997.
English Abstract of JP02-126184 Published May 15, 1990.
English Abstract of JP02-182267 Published Jul. 16, 1990.
English Abstract of JP4-224764 Published Aug. 14, 1992.
English Abtsract of JP4-507059 Published Dec. 10, 1992.
English Abstract of JP2006250582 Published Sep. 21, 2006.
English Abstract of JP3017167 Published Nov. 30, 1999.
English Abstract of JP56-163486 Published Dec. 16, 1981.
English Abstract of JP 7-500039 Published Mar. 14, 1994.
English Abstract of RU2091087.
English Abstract of RU2212254.
Annersten, M. et al., Insulin Pens Dribble From the Tip of the Needle After Injection, Practical Diabetes Int., vol. 17(4), pp. 109-111 (2000).
Beckmann, Sensors, Memory, Circuits, Polyapply Newsletter, vol. 1(3), (2006).
Common Insulin Injection Challenges:lhttp://www.bd.com/us/diabetes/page.aspx?cat=7001 &ID=7265.
Gnanalingham, M.G. et al., Accuracy and Reproducibility of Low Dose Insulin Administration Using Pen-Injectors and Syringes, Downloaded From adc.bmj.com on Jan. 9, 2008.
Owen Mumford Product Range.
Search Report Issued in Connection With PCT Appln. No. PCT/EP2007/052630, Mailed Nov. 12, 2007.
Search Report Issued in Connection With European Application No. 06005599.3, Mailed Oct. 4, 2006.
Search Report Issued in Connection With PCT Application No. PCT/EP2007/052633, Mailed Feb. 20, 2008.
Search Report Issued in Connection With European Appln No. 06005602.5, Mailed Oct. 16, 2006.
Trankler, Hans-Rolf, R. Oldenbourg, Verlag, Munchen, Wien.
Notice of Opposition by Owen Mumford (UK).
Notice of Opposition by Genentech (USA).
Notice of Opposition by Techpharma (CH) Including English Translation.
Opposition in Related European Patent Application EP 02711784.5 of Sep. 19, 2008.
Validity Opinion by the UK PTO.
Answer in *Novo Nordisk A/S v. Sanofi-Aventis U.S. LLC* and Sanofi-Aventis downloaded from PACER on Feb. 29, 2008.
Chia Kai Su et al, Process Biochemistry, 2006, vol. 41, Part 2, pp. 257-263.
Complaint in *Novo Nordiks A/S v. Sanofi-Aventis U.S. LLC* and Sanofi-Aventis downloaded from PACER on Feb. 29, 2008.
Declaration of Benard Sams in *Novo Nordisk A/S v. Sanofi-Aventis U.S. LLC* and Sanofi-Aventis downloaded from PACER on Jul. 29, 2008.
Dennison, Clive et al, Protein Expression and Purification, 2004, vol. 11, Part 2, pp. 149-161.
English Abstract of JP06-034825, Published Feb. 10, 1994, Shyoudenshiya:KK et al.
English Abstract of JP06-055644, Published on Jan. 3, 1994, Sekisui Chem. Co. LTD.
English Abstract of JP06-296691, Published on Oct. 25, 1994, Michel et al.
English Abstract of JP57-000033, Published on Jan. 5, 1982, Sanyo Electric Co.
English Abstract of JP64-035671, Published on Jun. 2, 1989, Applicant is Pentel KK.
English Abstract of JP2000-237308, Published on Sep. 5, 2000, Applicant is CKD Corp.
English Abstract of JP2003-284777, Published on Oct. 7, 2003, Applicant is Suugan KK.
English Language Abstract of French Patent No. 2697434, published on May 16, 1994, Applicant is Godillon Jean-Francois.
English Language Abstract of French Patent No. 2767479, published on Feb. 26, 1999, Applicant is Aguettant Lab.
English Language Abstract of German Patent No. 3048135, published on Jul. 15, 1982, Applicant is Imed Corp.
English Language Abstract of German Patent No. 4419235, published on Dec. 7, 1995, Applicant is Braeger.
Fransson et al, Pharmaceutical Research, 1997, vol. 14, Part 5, pp. 606-612.
International Search Report and Written Opinion issued in connection with counterpart PCT Application No. PCT/EP2006/061747, mailed Sep. 29, 2006.
Leonil et al, Enzyme and Microbiol Technology, 1994, vol. 16, Part 7, pp. 591-595.
Machine translation of EP679440TX, Published on Nov. 2, 1995, Applicant is Eppendorf-Netheler-HinzGMBH.
Machine translation of FR2583291TX, Published on Dec. 19, 1986, Applicant is Hazon.
May 17, 2002 Office Action in 09768760 filed on Jan. 24, 2001 by Hansen et al.
Search Report issued in connection with counterpart Danish Application No. PA 2005 00588, filed on Oct. 18, 2007 by Glejbol et al. mailed Feb. 13, 2006.
Opinion of US District Court for the District of NJ (Docket No. 3:07-cv-03206-MLC-JJH in *Novo Nordisk A/S v. Sanofi-Aventis U.S. LLC* and Sanofi-Aventis Denying motion of a preliminary injunction entered Feb. 20, 2008.
U.S. Appl. No. 10/610,926 which is owned by the same assignee as U.S. Appl. No. 11/765,789, filed on Jun. 20, 2007 by Moller et al.
Paule, B.J.A. et al, Protein Expression and Purification, 2004, vol. 34, Part 2, pp. 311-316.
Final Office Action mailed Apr. 14, 2006 in U.S. Appl. No. 10/646,295, filed Aug. 22, 2003 by Hansen et al.
Final Office Action mailed Feb. 8, 2005 in U.S. Appl. No. 10/646,295, filed Aug. 22, 2003 by Hansen et al.
Final Office Action mailed Sep. 29, 2009.in U.S. Appl. No. 11/911,869, filed May 21, 2008 by Gleibol et al.

Notice of Allowance Action mailed Sep. 26, 2006.in U.S. Appl. No. 10/646,295, filed Aug. 22, 2003 by Hansen et al.
Non-final Office Action mailed Aug. 29, 2005. in U.S. Appl. No. 10/646,295, filed Aug. 22, 2003 by Hansen et al.
Non-final Office Action mailed Jan. 8, 2009 in U.S. Appl. No. 11/911,869, filed May 21, 2008 by Glejbol et al.
Non-final Office Action mailed Apr. 1, 2009.in U.S. Appl. No. 11/911,871, filed Jun. 19, 2008 by Glejbol et al.
Final Action mailed Nov. 5, 2009. in U.S. Appl. No. 11/122,289, filed May 4, 2005 by Moller et al.
Non-final Office Action mailed Mar. 17, 2008 in U.S. Appl. No. 11/122,289, filed May 4, 7005 by Moller et al.
Final Action mailed Nov. 5, 2009 in U.S. Appl. No. 11/765,789, filed Jun. 20, 2007 by Moller et al.
Non-final Office Action mailed Dec. 17, 2008 in U.S. Appl. No. 11/765,789, filed Jun. 20, 2007 by Moller et al.
Non-final Office Action mailed Mar. 14, 2008 in U.S. Appl. No. 11/765,789, filed Jun. 20, 2007 by Moller et al.
Final Action mailed Jan. 15, 2010 in U.S. Appl. No. 11/931,010, filed Oct. 31, 2007 by Moller et al.
Non-final Office Action mailed from the USPTO on Apr. 2, 2009 in U.S. Appl. No. 11/931,010, filed Oct. 31, 2007 by Moller et al.
Reissue U.S. Appl. No. 10/442,855, filed May 21, 2003 by Steenfeldt-Jensen.
Reissue U.S. Appl. No. 10/960,900, filed Oct. 7, 2004 by Steenfeldt-Jensen.
Reissue U.S. Appl. No. 11/121,331 filed May 3, 2005 by Steenfeldt-Jensen.
Reissue U.S. Appl. No. 11/640,610, filed Dec. 18, 2006 by Steenfeldt-Jensen.
Written Opinion issued in connection with counterpart PCT Application No. PCT/EP7006/061747 mailed Nov. 8, 2006.
Advisory Action mailed on Mar. 23, 2010 in U.S. Appl. No. 11/122,289, filed May 4, 2005 by Moller et al.
International Search Report and Written Opinion Issued in Connection With Counterpart PCT Application No. PCT/EP2006/061748, Mailed Aug. 10, 2006.
Search Report Issued in Connection With Counterpart Danish Application No. PA 2005 00589, Mailed Feb. 16, 2006.
Written Opinion Issued in Connection With Counterpart PCT Application No. PCT/EP2006/061748, Mailed Nov. 8, 2006.
Non-Final Rejection of Oct. 7, 2008 in U.S. Appl. No. 10/508,104 (US Patent No. 7,678,084; Issue Date Mar. 16, 2010) Filed Sep. 15, 2004; First Named Inventor: Jared Alden Judson.
Non-Final Rejection of Mar. 19, 2009 in U.S. Appl. No. 10/508,104 (US Patent No. 7,678,084; Issue Date Mar. 16, 2010) Filed Sep. 15, 2004; First Named Inventor: Jared Alden Judson.
Office Action Mailed Mar. 17, 1999 in U.S. Appl. No. 08/973,109, filed Jun. 3, 1996 by Klitmose.
Notice of Allowance Mailed Oct. 25, 1999 in U.S. Appl. No. 08/973,109, filed Jun. 3, 1996 by Klitmose.
Office Action Mailed Apr. 26, 1999 in U.S. Appl. No. 09/090,144, filed Jun. 4, 1998 by Klitmose.
Final Action Mailed Dec. 20, 1999 in U.S. Appl. No. 09/090,114, filed Jun. 4, 1998 by Klitmose.
Notice of Allowance Mailed Apr. 6, 2004 in U.S. Appl. No. 09/090,144, filed Jun. 4, 1998 by Klitmose.
Non-Final Office Action Mailed Aug. 27, 2002 in U.S. Appl. No. 09/882,536, filed Jun. 14, 2001 by Moller et al.
Notice of Allowance Mailed Jun. 17, 2003 in U.S. Appl. No. 09/882,536, filed Jun. 4, 2001 by Moller et al.
Notice of Allowance Mailed on Apr. 23, 2007 in U.S. Appl. No. 10/667,040, filed Sep. 22, 2003 by Moller et al.
Non-Final Rejection Mailed on Dec. 15, 2008 in U.S. Appl. No. 11/122,289, filed May 4, 2005 by Moller et al.
Advisory Action Mailed on Mar. 25, 2010 in U.S. Appl. No. 11/122,289, filed May 4, 2005 by Moller et al.
Office Action Mailed on Jan. 15, 2010 in 11/930,926, filed Oct. 31, 2007 by Moller et al.
Final Action Mailed on Jan. 15, 2010 in U.S. Appl. No. 11/930,926, filed Oct. 31, 2007 by Moller et al.
Office Action Mailed on Sep. 15, 2004 in U.S. Appl. No. 10/646,295, filed Aug. 22, 2003 by Hansen et al.
Advisory Action Mailed Jul. 1, 2005 in U.S. Appl. No. 10/646,295, filed Aug. 22, 2003 by Hansen et al.
Abandonment Mailed on Oct. 8, 2009 in U.S. Appl. No. 11/911,869, filed Oct. 18, 2007 by Glejbol et al.
Office Action Mailed on Apr. 1, 2009 in U.S. Appl. No. 11/911,871, filed Oct. 18, 2007 by Glejbol et al.
Abandonment Mailed on Nov. 6, 2009 in U.S. Appl. No. 11/911,871, filed Oct. 18, 2007 by Glejbol et al.
Office Action Mailed on Jun. 8, 2010 in U.S. Appl. No. 12/571,72, filed Oct. 1, 2009 by Glejbol et al.
Office Action Mailed Jul. 20, 2010 in U.S. Appl. No. 12/300,675, filed May 3, 2007 by Moller et al.
Print-out of file history of U.S. Appl. No. 10/610,926 which is owned by the same assignee as U.S. Appl. No. 11/122,289 and U.S. Appl. No. 11/765,789.
Rose, Keith et al., Bioconjugate Chemistry, "Natural Peptides As Building Blocks for the Synthesis of Large Protein-Like Molecules With Hydrazone and Oxime Linkages", 1996, vol. 7, 2, pp. 552-556.
Yurkovetskiy, A. et al., Biomacromolecules., "Fully Degradable Hydrophilic Polyals for Protein Modification", 2005, vol. 6, 5, pp. 2648-2658.

* cited by examiner

INJECTION DEVICE

CROSS REFERENCE TO RELATED APPLICATIONS

This application is a continuation of application Ser. No. 11/765,789 filed on Jun. 20, 2007, which is a continuation of application Ser. No. 10/667,040 filed on Sep. 22, 2003, which is a continuation of application Ser. No. 09/882,536 filed on Jun. 14, 2001 and claims priority under 35 U.S.C. 119 of Danish application nos. PA 2000 00932 and PA 2001 00372 filed on Jun. 16, 2000 and Mar. 7, 2001 respectively, and U.S. provisional application Nos. 60/214,470 and 60/275,790 filed on Jun. 27, 2000 and Mar. 14, 2001 respectively. The benefit of application Ser. Nos. 11/765,789 filed on Jun. 20, 2007; 10/667,040 filed on Sep. 22, 2003; 09/882,536 filed on Jun. 14, 2001 in the U.S. is claimed under 35 U.S.C. 120, the contents of which are fully incorporated herein by reference.

BACKGROUND OF THE INVENTION

The invention relates to syringes by which a dose can be set by rotating a dose setting member and by which an injection button elevates from an end of the syringe a distance proportional to the set dose and wherein the set dose can be injected by pressing home the injection button to its not elevated position.

An almost classic pen of this type is described in EP 327 910.

By setting a dose on this pen a tubular member forming an injection button is screwed up along a threaded piston rod a distance corresponding to the distance said piston rod must be moved to inject the set dose. The tubular member simply forms a nut which is during the dose setting screwed away form a stop and which is during the injection pressed back to abutment with said stop and the force exerted on the button is directly transmitted to the a piston closing one end of an ampoule in the syringe which ampoule contains the medicament to be injected. When the piston is pressed into the ampoule the medicament is pressed out through a needle mounted through a closure at the other end of the ampoule.

By time it has been wanted to store larger amount in the ampoules, typically 3 ml instead of 1.5 ml. As it has not been appropriate to make the syringe longer the ampoule is instead given a larger diameter, i.e. the area of the piston facing the medicament in the ampoule has been doubled and consequently the force which has to be exerted on the piston to provide the same pressure as previously inside the ampoule has been doubled. Further the distance the piston has to be moved to inject one unit of the medicament has been halved.

This development is not quite favourable, as especially users having reduced finger strength have their difficulties in pressing the injection button, a problem that is further increased when still thinner needles are used to reduce the pain by injection. Also with quite small movements of the button it is difficult to feel whether the button is moved at all and by injection of one unit from a 3 ml ampoule the piston and consequently the injection button has to be moved only about 0.1 mm.

Consequently a wish for a gearing between the injection button and the piston has occurred so that the button has a larger stroke than has the piston. By such a gearing the movement of the injection button is made larger and the force, which has to be exerted on the injection button, is correspondingly reduced.

In EP 608 343 a gearing is obtained by the fact that a dose setting element is screwed up along a spindle having a thread with a high pitch. When said dose setting element is pressed back in its axial direction the thread will induce a rotation of said dose setting element, which rotation is via a coupling transmitted to a driver nut with a fine pitch which driver nut will force a threaded not rotatable piston rod forward.

A similar gearing is provided in WO 99/38554 wherein the thread with the high pitch is cut in the outer surface of a dose setting drum and is engaged by a mating thread on the inner side of the cylindrical housing. However, by this kind of gearing relative large surfaces are sliding over each other so that most of the transformed force is lost due to friction between the sliding surfaces. Therefore a traditional gearing using mutual engaging gear wheels and racks is preferred.

From WO 96/26754 is known an injection device wherein two integrated gear wheels engages a rack fixed in the housing and a rack inside a plunger, respectively. When the plunger is moved axially in the housing the rack inside this plunger can drive the first gear wheel to make the other integral gear wheel move along the fixed rack in the housing. Thereby the gear wheel is moved in the direction of the plunger movement but a shorter distance than is this plunger and this axial movement of the integrated gear wheels is via a housing encompassing said gear wheels transmitted to a piston rod which presses the piston of an ampoule further into this ampoule. However, the rack inside the plunger is one of a number axial racks provided inside said plunger. These racks alternates with untoothed recesses, which allow axial movement of the plunger without the first gear wheel being in engagement with a rack in this plunger. This arrangement is provided to allow the plunger to be moved in a direction out of the housing when a dose is set. When the plunger is rotated to set a dose it is moved outward a distance corresponding to one unit during the part of the rotation where the first gear wheel passes the untoothed recess, thereafter the first gear wheel engages one of the racks so the set unit can be injected, or the rotation can be continued to make the first gear wheel pass the next recess during which passing the set dose is increased by one more unit and so on until a dose with the wanted number of units is set.

A disadvantage by this construction is that the teeth of the racks and gearwheels alternating have to be brought in and out of engagement with each other with the inherit danger of clashing. As only a few racks separated by intermediary untoothed recess can be placed along the inner surface of the plunger only few increments can be made during a 360 degree rotation.

SUMMARY OF THE INVENTION

It is an objective of the invention to provide an injection device, which combines the advantages of the devices according to the prior art without adopting their disadvantages and to provide a device wherein is established a direct gearing, i.e. a gearing by which more transformations of rotational movement to linear movement and linear movement to rotational movement are avoided, between the injection button and the piston rod.

This can be obtained by an injection device comprising a housing wherein a piston rod threaded with a first pitch is non rotatable but longitudinally displaceable guided, a nut engaging the thread of the piston rod which nut can be screwed along the threaded piston rod away from a defined position in the housing to set a dose and can be pressed back to said defined position carrying the piston rod with it when the set dose is injected, a dose setting drum which can be screwed outward in the housing along a thread with a second pitch to lift an injection button with it up from the proximal end of the housing, which injection device is according to the invention characterised in that a gearbox is provided which provides a gearing between the axial movements of the injection button and the nut relative to the housing which gearing has a gearing ratio corresponding to the ratio of said second and first pitch.

In a preferred embodiment the gearing between the movements of the injection button and the nut is obtained by the gearbox comprising at least one gear wheel carried by a connector which projects from the gear box longitudinally displaceable but non rotatable relative to said gearbox and is integral with the nut, a first rack integral with a first element of the gearbox, which element is rotational but not longitudinally displaceable relative to the housing, and second element carrying a second rack projecting from said gearbox longitudinally displaceable but non rotatable relative to said first element and being coupled to the injection button to follow longitudinal movements of said button, the at least one gear wheel engaging the first and the second rack, respectively, and being dimensioned to provide a gearing by which a longitudinal movement of the second rack is transformed to a longitudinal movement of the connector with a gearing ratio for the mentioned longitudinal movements of the second rack and the connector relative to the housing, which gearing ratio corresponds to the ratio of said second to said first pitch.

In such a device only the forces necessary to drive the dose setting drum are transformed by a thread with a high pitch whereas the forces necessary to move the piston by injection is transmitted to said piston through a conventional gear with constantly engaging gears and racks.

The piston rod is provided with a stop for the movement of the nut along the thread of said piston rod. This way a dose setting limiter is provided in the classic way, which involves no additional members to prevent setting of a dose exceeding the amount of liquid left in the ampoule.

In the following the invention is described in further details with references to the drawing, wherein

DETAILED DESCRIPTION

Figure 1:
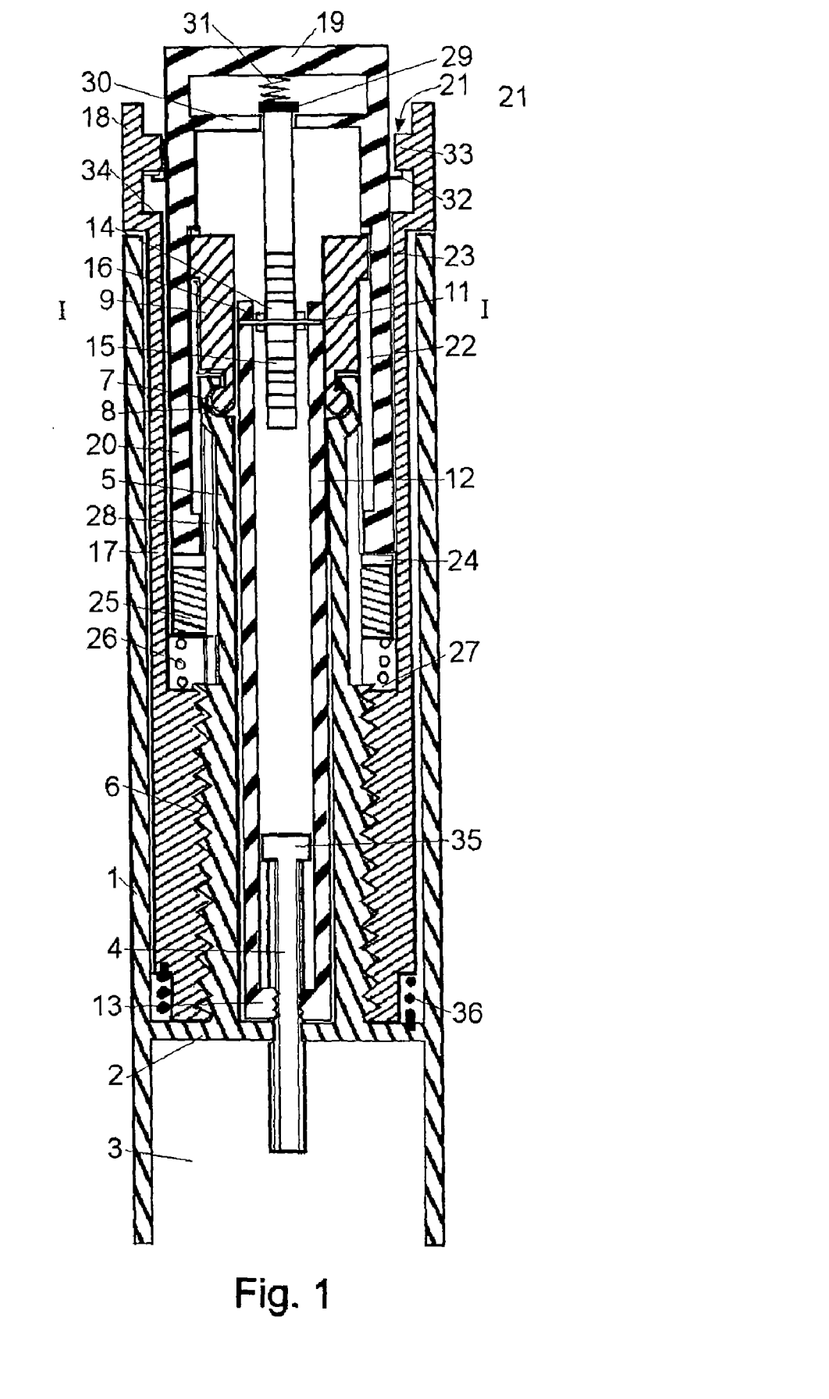
FIG. 1 schematically shows a sectional view of an injection device according to the invention.

In the device shown in FIG. 1 an elongated cylindrical housing 1 has a partitioning wall 2 which divides the housing in a compartment containing a dose setting mechanism and a compartment 3 designed for the accommodation of a not shown ampoule. A threaded piston rod 4 has a not round cross section by which it fits through a central opening in the wall 2 so that the piston rod 4 can be displaced longitudinally through the central opening in the wall 2 but not rotated relative to this wall.

Concentrically with the housing 1 the wall 2 carries on its side turning away from the compartment 3 a tubular element 5 which is at a part of it adjacent to the wall 2 provided with an outer thread 6 and which has at its free end a circumferential recess 7. A ring shaped coupling element 8 on a gear box 9 engages the recess 7. By this coupling the gearbox is fixed in the housing 1 in a way that allows the gearbox 9 to rotate in the housing but not to be axially displaced relative to said housing.

In the gearbox 9 a gear wheel assembly comprising two integral gear wheels is journaled on a shaft 11, which runs perpendicular to the longitudinal axis of the device between two axial connection bars 12. The connection bars 12 project from the gear box towards the partition wall 2 and are connected to a nut 13 which adjacent to the wall 2 engages the thread of the piston rod 4. The gear wheel assembly comprises a gear wheel 14 with a large diameter engaging the teeth of a rack 15 which is guided in the gear box to be displaced in the longitudinal direction of the device, and a gear wheel 16 with a small diameter engaging a rack 10 in FIG. 2 extending in the longitudinal direction of the device on the inner wall of the gearbox 9. The gear wheel 16 with the small diameter may be divided into two gear wheels placed on each side of the of the gear wheel 14, and the rack on the inner wall of the gearbox 9 may have a longitudinal recess without any teeth to make room for the gear wheel 14.

A tubular dose setting drum 17 fitting into the housing 2 is at an end provided with an internal thread mating and engaging the outer thread 6 of the tubular element 5 and has at its other end a part with enlarged diameter forming a dose setting button 18. Due to the engagement with the thread 6 the dose setting drum 17 may be screwed in and out of the housing to show a number on a not shown helical scale on its outer surface in a not shown window in the housing 1.

A bottom 19 in a deep cup shaped element, which has a tubular part 20 fitting into the dose setting drum 17 and encompassing the gearbox 9, forms an injection button. Coupling means between the dose setting drum 17 and the cup shaped element ensures that rotation of the dose setting drum 17 is transmitted to the cup shaped element. Further the inner wall of the tubular part 20 has longitudinal recesses 22 engaged by protrusions 23 on the gearbox 9 so that rotation of the dose setting drum 17 via the cup shaped element is transmitted to the gearbox 9.

At the edge of the open end of the cup shaped element a rosette of V-shaped teeth are provided, which teeth engage a corresponding rosette of V-shaped teeth 24 on a ring 25 which is pressed against the edge of the cup shaped element by a spring 26 which is compressed between a not toothed side of the ring 25 and a round going shoulder 27 on the inner wall of the dose setting drum 17 at an inner end of the inner thread of this drum. The ring is provided with an inner recess, which is engaged by a longitudinal rib 28 on the tubular element 5 so that the ring 25 can be displaced in the axial direction of the device but cannot be rotated relative to the housing 1. Thereby a click coupling is established which makes a click noise when the V-shaped teeth at the edge of the cup shaped element by rotation of this element rides over the V-shaped teeth of the ring 25.

A head 29 on the projecting end of the rack 15 is with a play fixed at the bottom of the cup shaped element between the bottom 19 forming the injection button and an inner wall 30 near this bottom. The rack is fixed in a position with its head pressed against the wall 30 by a spring 31 between the bottom 19 and the head 29.

To set a dose the dose setting button 18 is rotated to screw the dose-setting drum 17 up along the thread 6. Due to the coupling 21 the cup shaped element will follow the rotation of the dose-setting drum 17 and will be lifted with this drum up from the end of the housing 1. By the rotation of the cup shaped element the V-shaped teeth 24 at the edge of its open end will ride over the V-shaped teeth of the non rotatable ring 25 to make a click sound for each unit the dose is changed. A too high set dose can be reduced by rotating the dose setting button 18 in the opposite direction of the direction for increasing the dose. When the dose setting drum is screwed up along the thread 6 on the tubular element 5 the ring 25 will follow the dose setting drum in its axial movement as the spring 26 is supported on the shoulder 27. The spring will keep the V-shaped teeth of the ring 25 and the cup shaped element in engagement and maintain in engagement the coupling 21, which may comprise A-shaped protrusions 32 on the cup shaped element engaging A-shaped recesses in an inner ring 33 in the dose setting button 18.

The rotation of the dose setting button 18 and the cup shaped element is further transmitted to the gearbox 9 through the protrusions 23 on this gearbox engaging the longitudinal recesses 22 in the inner wall of the tubular part 20 of said cup shaped element. The rotation of the gearbox 25 is through the connection bars 12 transmitted to the nut 13, which is this way screwed up along the thread of the piston rod 4 and lifted away from its abutment with the wall 2 when a dose it set. As the dose is set by moving the nut 13 on the very piston rod which operates the piston in the not shown ampoule in the compartment 3 a dose setting limiter, which ensures that the size of the set dose does not exceed the amount of medicament left in the ampoule, can easily be established by providing the piston rod 4 with a stop 35 which limits the movement of the nut 13 up along the piston rod 4.

Due to the confinement of the head 29 in the space between the bottom 19 and the wall 30 of the cup shaped element, the rack 15 is drawn with the injection button outward. Also the axial movement of the nut 13 relative to the housing 1 will be transmitted to the gear wheel assembly through the connection bars 12 and this movement will through the gearbox induce an outward movement of the rack 15. This induced outward movement have to be the same as the outward movement induced by outward movement of the injection button. This is obtained by dimensioning the gear wheels of the gearbox 9 so that the gear ratio for the movements of the connection bars 12 and the rack 15 relative to the housing corresponds to the ratio of the pitches for the thread on the piston rod and for the thread 6 for the longitudinal movement of the dose setting drum 17.

To inject a set dose the injection button is pressed by pressing on the bottom 19. In the initial phase of the pressing the spring 31 is compressed where after the pressing force is directly transmitted to the head 29 of the rack 15 and this way to the rack 15 itself. Through the gear box 9 the force is transformed and is transmitted through the connection bars 12 to the nut 13 which will press the piston rod 4 into the compartment 3 until the dose-setting drum 17 abuts the wall 2.

During the initial phase of the movement of the injection button the A-shaped protrusions 32 on the cup shaped element will be drawn out of their engagement with the A-shaped recesses in the ring 33. The dose-setting drum 17 can now rotate relative to the injection button and will do so when the A-shaped protrusions 32 press against a shoulder 34 at the bottom of the dose setting button 18. Only a force sufficient to make the dose setting drum rotate to screw itself downward along the thread 6 is necessary as the force necessary to make the injection is transmitted to the piston rod 4 through the gearbox 9. A helical reset spring 36 concentric with the dose setting drum can be mounted at the lower end of this drum and can have one end anchored in the dose setting drum 17 and the other end anchored in the wall 2. During setting of a dose this spring may be tighter coiled so that on the dose setting drum it exerts a torque approximately corresponding to the torque necessary to overcome the friction in the movement of the dose setting drum along the thread 6 so that the force which the user have to exert on the injection button is only the force necessary to drive the piston rod into an ampoule to inject the set dose.

Figure 2:
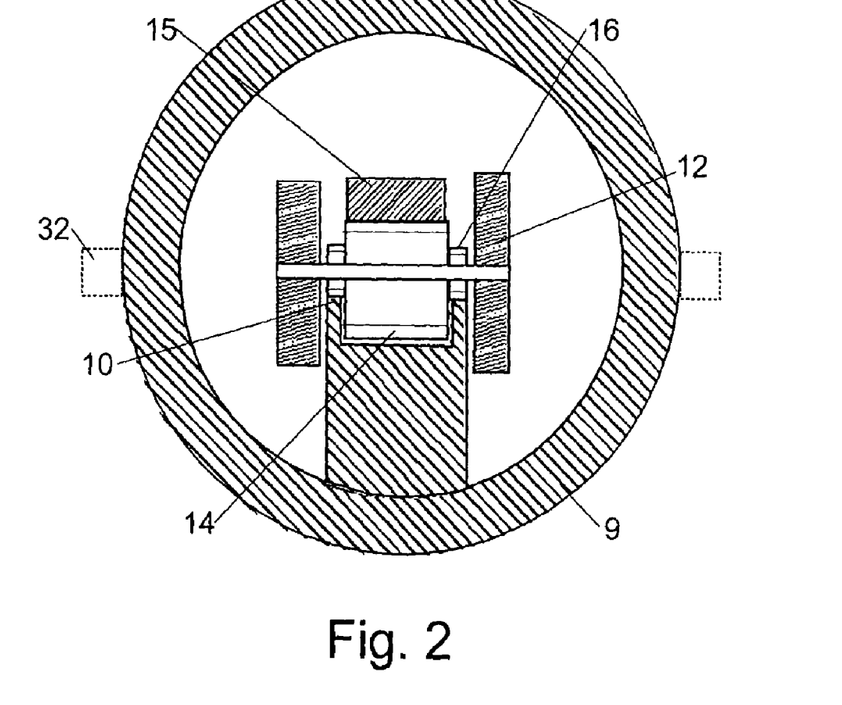
FIG. 2 shows schematically a sectional view of the gear box along the line I-I in FIG. 1.

It shall be noticed that use of only one size gear wheel which engages as well the rack 15, which is movable relative to the gear box 9, as the rack 10, which is unmovable relative to the gear box, provides a gearing ratio of 2:1 for the longitudinal movement relative to the syringe housing 1 for the movable rack 15 and the connector 12, which carries the shaft 11 of the gear wheel.

Figure 3:
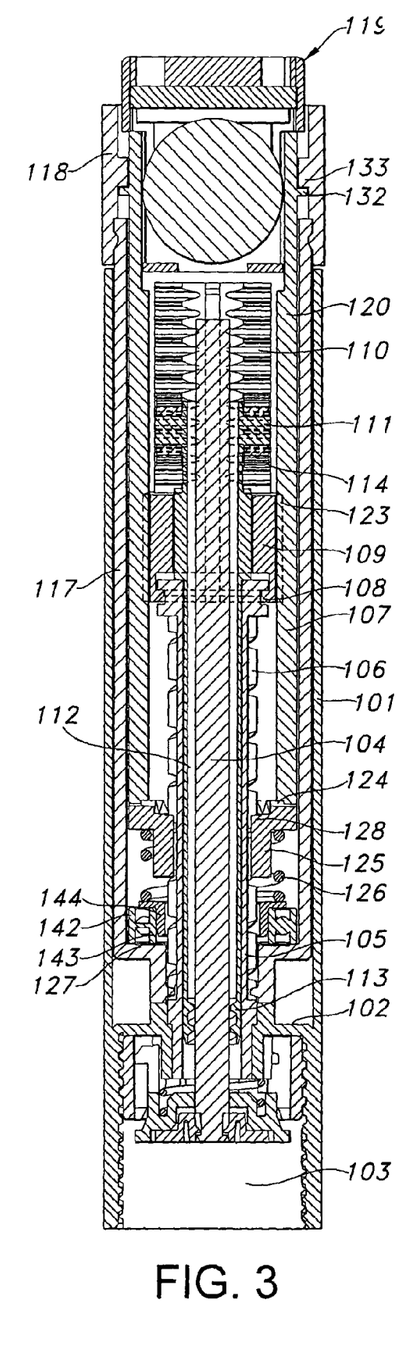
FIG. 3 shows a longitudinal sectional view in the dose setting part of another embodiment of an injection device according to the invention.
Figure 4:
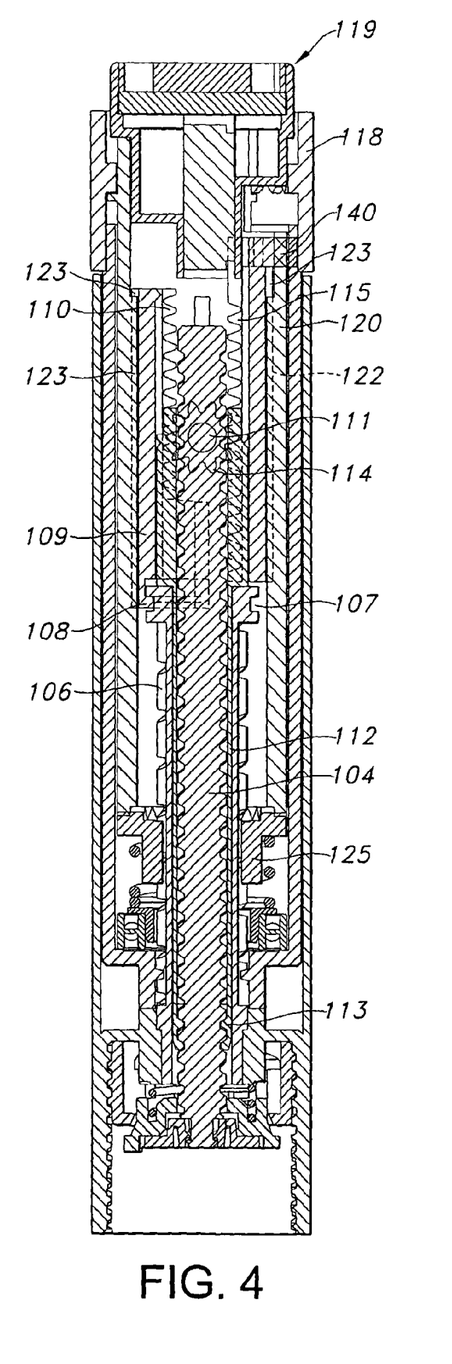
FIG. 4 shows a longitudinal sectional view perpendicular to the view in FIG. 3.
Figure 5:
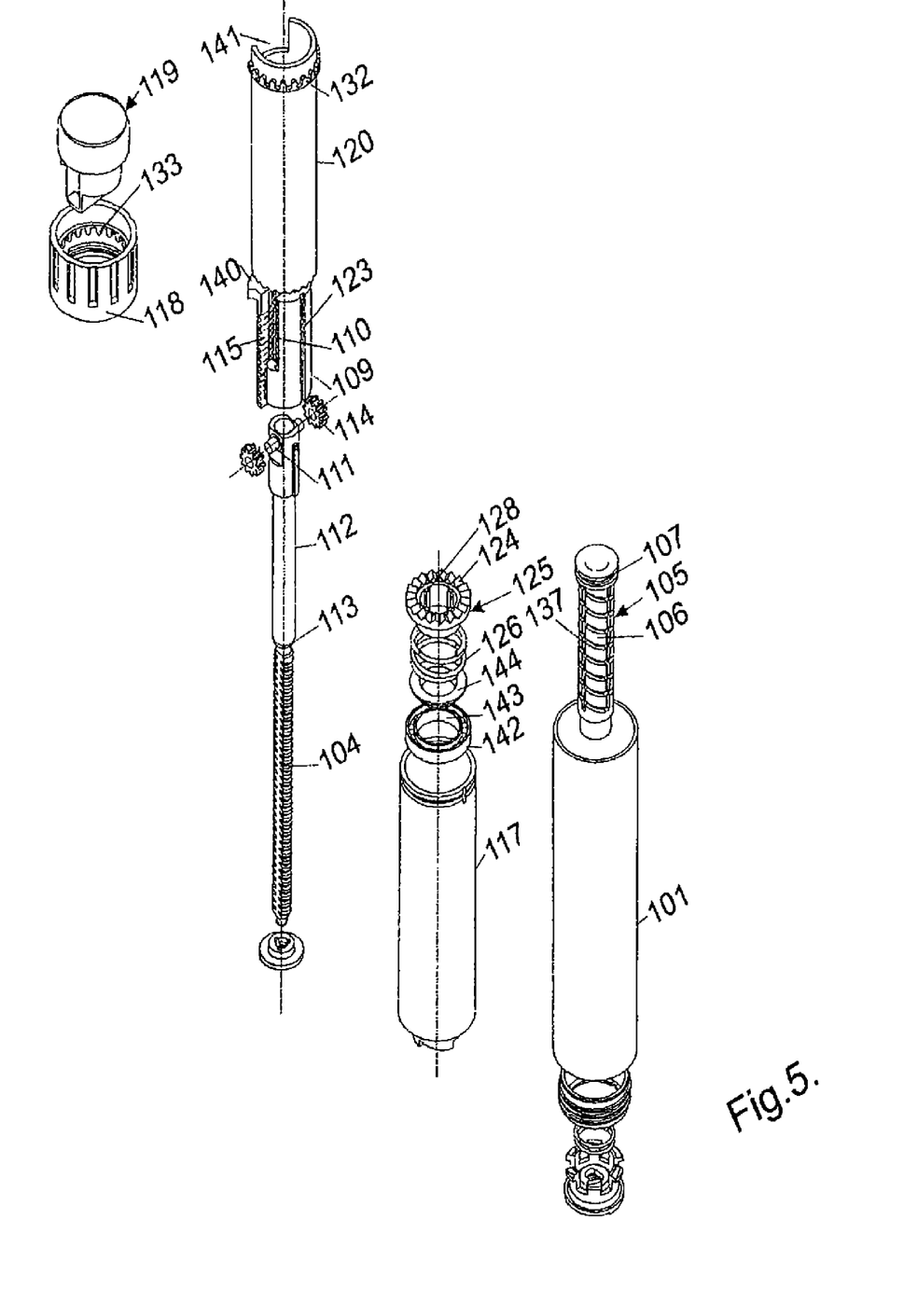
FIG. 5 shows an exploded picture of the of the device shown in FIGS. 3 and 4.

FIGS. 3 and 4 shows a preferred embodiment wherein only one size gear wheel is used and wherein elements corresponding to elements in FIGS. 1 and 2 are given the same references as these elements with a prefixed "1".

For manufacturing reasons minor changes are made. So the partitioning wall 102 and the tubular element 105 are made as two parts which are by the assembling of the device connected to each other to make the assembled parts act as one integral part. The same way the dose setting drum 117 and the dose setting button 118 are made as two parts, which are fixed firmly together.

A circumferential recess 107 is provided as an outer recess at the free end of the tubular part 105 and a ring shaped coupling element is provided as an inner bead 108 on the gearbox element 109 which bead engages the recess 107 to provide a rotatable but not axially displaceable connection between the tubular part 105 and the gearbox.

A tubular element 120 having ridges 122 which engages recesses 123 on the gearbox is at its upper end closed by a button 119 from which a force provided by pressing this button is transmitted to the tubular element 120.

The gearbox is formed by two shells, which together form a cylinder fitting into the tubular element where the shells are guided by the engagement between the ridges 122 and the recesses 123. Racks 110 and 115 are provided along edges of the shells facing each other. One shell forming the gearbox part 109 is provided with the inner bead 108, which engages the circumferential recess 107 at the end of the central tubular part 105 and carries the rack 110. The other shell is axially displaceable in the tubular element 120 and forms the rack 115. At its outer end projecting from the gearbox the shell carrying the rack 115 is provided with a flange 140 which is positioned in a cut out 141 in the end of the tubular element 120 carrying the button 119 so that this button and the tubular element 120 can be moved so far inward in the device that the engagement of the teeth 132 and 133 can be released before the button 119 abuts the flange 140.

A tubular connection element 112 connects the threaded piston rod 104 with the gearbox. At its end engaging the piston rod 104 the connection element has a nut 113 with an internal thread mating the external thread of the piston rod. At its end engaging the gear box the connection element is provided with two pins 111 projecting perpendicular to the longitudinal axis of the connection element 112 at each side of this element. Each pin 111 carries a gear wheel 114 which is placed between and engages the two racks 110 and 115.

This way the connection element 112 will be rotated with the gear box but can be displaced axially relative to said gear box when the racks 110 and 115 are moved relative to each other. In practice it will be the rack 115, which is moved relative to the gearbox element 109 and the housing and will by the shown construction result in a movement of the connection element 112 relative to housing a distance which is half the distance which the rack 115 is moved. A ring 125 which is at its periphery provided with a rosette of teeth 124 and has a central bore fitting over the central tube in the housing 101 so that this ring 125 can be axially displaced along said central tube 105, but internal ridges 128 in the central bore of the ring 125 engages longitudinal recesses 137 in the central tube to make the ring non rotatable in the housing so that a rosette of teeth at the edge of the tubular element 120 can click over the teeth 124 of the ring when said tubular element is rotated together with the dose setting drum 117. A spring 126 working between the ring 125 and an internal shoulder 127 provided in the dose setting drum 117 makes the ring follow the tubular element 120 when this element with the dose setting drum is moved longitudinally in the housing. To make the dose setting drum easy rotatable, especially when said dose setting drum is pressed inward in the housing, a roller bearing having an outer ring 142 supported by the shoulder 127 and an inner ring 143 supporting a pressure bushing 144 which supports the spring 126. By the provision of this smooth running support only very small axial forces are needed to rotate the dose setting drum 117 back to its zero position when a set dose is injected. This solution replaces the provision of a reset spring as the spring 36 in FIG. 1. The bearing is shown as a radial bearing but can be replaced by an axial bearing

I claim:

1. A method for expelling medication from a prefilled cartridge having an end closed by a piston wherein the cartridge is contained in an injection device having a rack and pinion gearbox assembly that couples an injection button with a piston driver; the method comprising the steps of:
   setting a dose to be injected from the prefilled cartridge;
   moving a first rack, which contains teeth, in a proximal direction, away from the cartridge and injecting end of the device during setting of a dose, the rack remaining in continuous meshed engagement with a pinion which during the setting of the dose causing the pinion to rotate in a first direction;
   moving the pinion in a proximal direction away from an injecting end of the device during the setting of the dose
   moving the first rack distally, which is toward, the injecting end of the device during injection of a dose and causing the pinion to rotate in an opposite direction and to move forward, thereby causing part of the transmission to drive the piston driver which in turn moves the piston within the cartridge and expels medication from the device.

2. The method of claim 1, further comprising the step of:
   rotating a second pinion at the same speed as the pinion of claim 1 during the expelling of the medication,
   wherein the second pinion is in continuous meshed engagement with a second rack.

3. The method of claim 2, wherein the first rack moves distally by a distance greater than the piston is driven distally during injection.

4. A method for injecting medication comprising the steps of:
   providing a medication delivery device having a housing for containing a prefilled cartridge of medication having a moveable piston at one end, wherein the device further comprises a plunger element (19) for receiving an injection force from a user, a gear set comprised of at least a first and second gear wheel that revolve around a common axis and wherein the first gearwheel is in continuous meshed engagement with a first toothed rack that is coupled to the plunger element so that the rack substantially moves in unison with the plunging element when it moves distally and proximally, wherein the second gear wheel is in continuous meshed engagement with a second rack;
   moving the plunger element proximally while setting a dose of medication to be injected from the cartridge;
   exerting a force on the plunger element in a distal direction, the force being large enough to drive the plunging element forward;
   moving the plunging element and the first rack in a distal direction as a result of the exerted force being applied to the plunging element;
   rotating the gear wheels as the first rack is moved distally;
   moving the gear wheels distally during injection when the plunging element is being depressed;
   moving the piston forward, wherein the piston moves a lesser distance than the first rack, wherein it moves the lesser distance as a result of a gearing created by the first and second racks and the first and second gear wheels.

5. A method for injecting a device that has a housing and contains a prefilled cartridge of medication, wherein the cartridge is closed at one end by a moveable piston, the method comprising the steps of:
   setting a dose by:
      moving a plunging rack in a proximal direction to set a dose to be injected;
         rotating a gear set comprised of at least one pinion gear wheel during dose setting wherein the pinion gear wheel is in continuous meshed engagement with the plunging rack
      injecting the set dose by:
         moving the plunging rack in a distal direction toward an injecting end of the device;
         causing the pinion gear wheel to rotate during movement of the plunging rack;
         transferring a force to a piston driver from the plunging rack through the gear set to a piston driver to expel medication;
      wherein the gear set moves longitudinally within the device during dose setting and dose injecting.

6. A method for injecting medication from a medication device have a housing and having a prefilled cartridge of medication which is closed at one end by a moveable piston, the method comprising the steps of:
   setting a dose of medication to be injected by rotating a dose scale drum away from an initial position to set the dose size;
   during rotation of the dose scale drum, moving a plunging rack that contains teeth in a proximal direction, which is away from the injecting end of the device;
   rotating a gear wheel during movement of the rack, the gear wheel being in constant meshed engagement with the plunging rack;
   moving the gear wheel proximally;
   moving the plunging rack distally;
   rotating the dose scale drum toward the initial position during the distal movement of the plunging rack so that the drum reaches the initial position upon completion of the injection.

* * * * *